United States Patent [19]

Bossard

[11] Patent Number: 4,818,945
[45] Date of Patent: Apr. 4, 1989

[54] NON CONTACTING VOLT METER

[75] Inventor: Peter R. Bossard, Langhorne, Pa.

[73] Assignee: Voyager Technologies, Inc., Langhorne, Pa.

[21] Appl. No.: 855,073

[22] Filed: Apr. 22, 1986

[51] Int. Cl.$^4$ .............................................. G01N 27/22
[52] U.S. Cl. ...................................... 324/457; 324/72; 324/76 R; 324/109
[58] Field of Search ................ 324/109, 72, 72.5, 457, 324/458, 118 R, 123 R, 76 R

[56] References Cited

U.S. PATENT DOCUMENTS 4,339,721 7/1982 Nihira et al. ......................... 324/458

FOREIGN PATENT DOCUMENTS 0124060 9/1981 Japan .................................... 324/457

OTHER PUBLICATIONS

Keyes, Vibrating Capacitor, 12/63, vol. 6, No. 7 p. 98.

Primary Examiner—A. D. Pellinen
Assistant Examiner—Leon K. Fuller
Attorney, Agent, or Firm—Marmorek, Guttman & Rubenstein

[57] ABSTRACT

A non contact voltmeter includes a multilayered structure adapted to configure a plurality of coupled capacitors in a manner to permit high speed operation. A high frequency input signal is applied to a plate capacitivity coupled to both the test object and a sensor. The structure is also configured to capacitivity couple the sensor directly to the test object. The structure allows for circuit configurations with low time constants permitting outputs at the input frequency as well as a small and inexpensive solid state configuration.

7 Claims, 2 Drawing Sheets

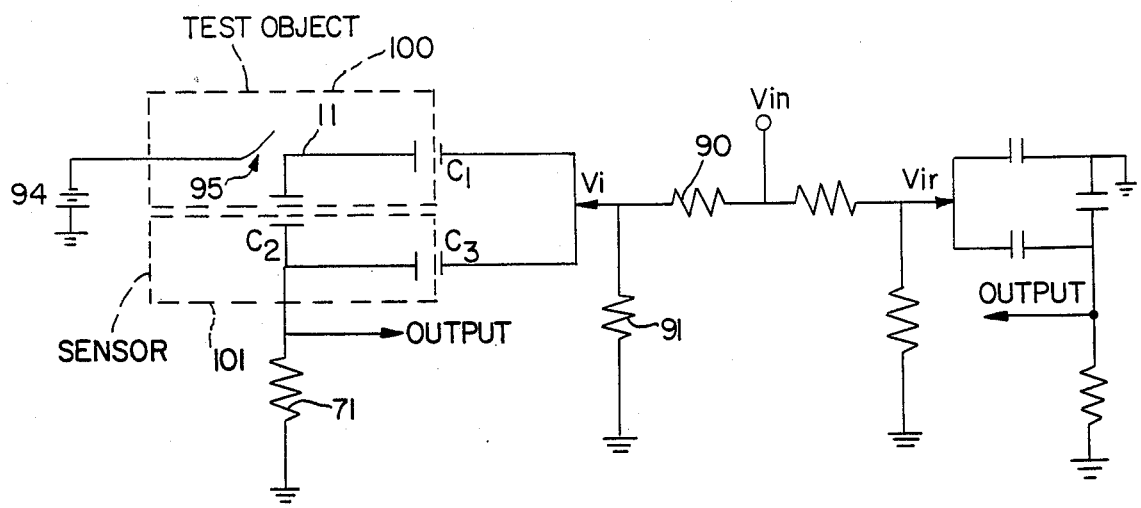
FIG. 4
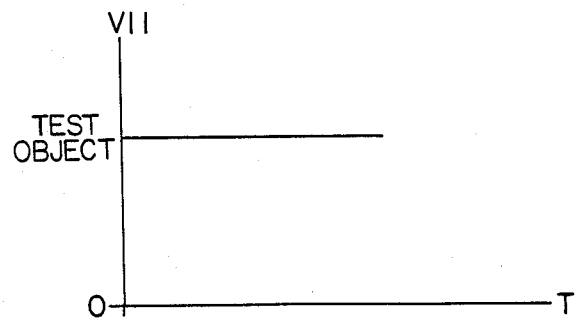
FIG. 5
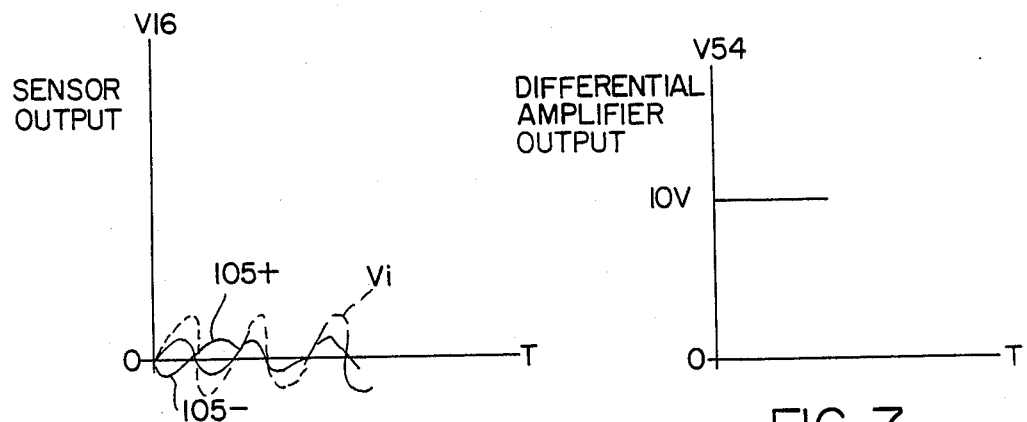
FIG. 6
FIG. 7

_NON CONTACTING VOLT METER_

FIELD OF THE INVENTION

This invention relates to volt meters and more particularly to non contact volt meters.

BACKGROUND OF THE INVENTION

Non contact volt meters are well known in the art. A typical non contact volt meter comprises a hand held package which includes a field sensing arrangement and a volt meter display operative to move a pointer to a voltage value representative of the field sensed.

Such a meter employs a capacitive sensor. The capacitor is exposed to a test object through a metallic layer which includes an aperture aligned with the capacitor. The time constant characteristic of the sensing electronics in such a meter is such that the frequency of operation is too low for many desirable applications.

In order to improve the frequency of operation, such meters are adapted to vary the separation between the test object and the sensor which, in fact, constitutes the two plates of the capacitor. This variation is implemented by fixing the sensor to a tuning fork. Frequencies on the order of one hundred Hertz are achieved in this manner. But such frequencies are still much lower than those required, for example, for sensing the voltage or charge on an electrostatic belt or drum typical of photocopy equipment.

Such meters, further, are quite bulky. Many potential uses for non contact volt meters allow little space for such equipment. A high speed and small non contact volt meter would find an eager market for many applications.

BRIEF DESCRIPTION OF THE INVENTION

In accordance with the principles of this invention, a non contact voltmeter comprises a lamellate structure comprising a plurality of operative layers electrically insulated from one another. The layers are designed to define an arrangement of three coupled capacitors. A first capacitor is formed between an input plate and a sensor plate to which an input signal is applied and an output signal is extracted respectively. Second and third capacitors are defined between the input plate and the test object and between the sensor plate and the test object. The resulting circuit arrangement exhibits low time constants which permit operation in the megahertz range well adapted for use, for example, in electrostatic copiers. Moreover, the structure is conveniently implemented with printed circuit (PC) technology to form a solid state configuration only a fraction of an inch on a side.

BRIEF DESCRIPTION OF THE DRAWING

FIG. 4 is a schematic circuit diagram of the structure of FIG. 1 and a similar reference structure; and FIGS. 5, 6 and 7 are plots of voltage versus time for a test surface, the output capacitor of the structure of FIG. 1 and the output of the circuits of FIGS. 2 or 4.

DETAILED DESCRIPTION

Figure 1:
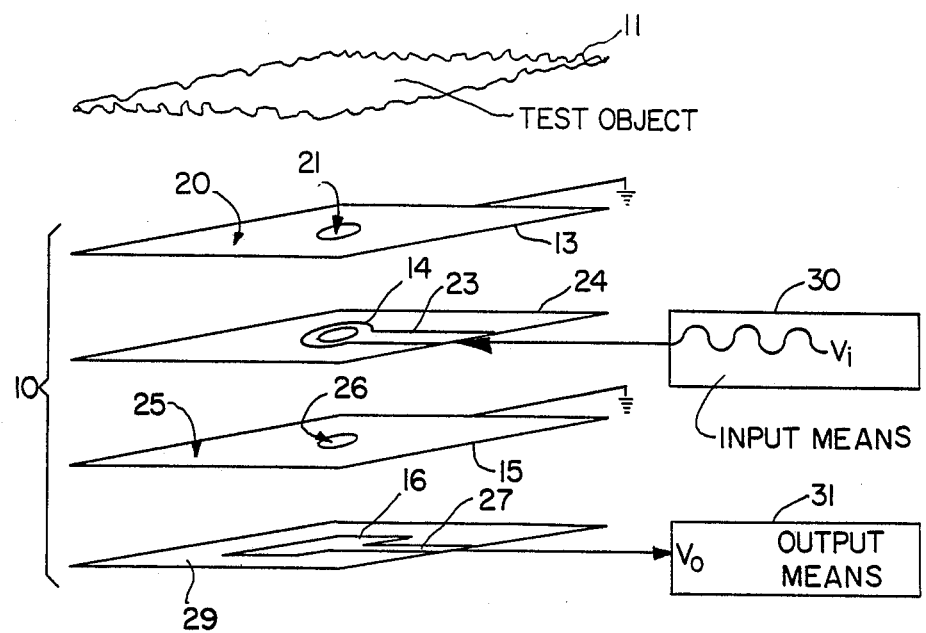
FIG. 1 is an exploded, plan view of a lamellate, non contact volt in accordance with the principle of this invention.

FIG. 1 shows a multilayered structure 10 adapted to measure the electric field emanating from a test object represented as a fragment 11 of some arbitrary object surface. The structure comprises four layers 13, 14, 15 and 16 from top to bottom as viewed in the figure. The top layer 13 comprises a layer of electrically insulating material with a metallized surface 20. The metallized surface includes an aperture 21 adapted to pass charged particles.

The second layer from the top, layer 14, comprises a metallic annulus adapted for external electrical interconnection by lead 23. The annulus is formed on insulating layer 24 and aligned with aperture 21 of layer 13. The next lower layer, layer 15, also comprises an electrically insulating layer with a metallized surface 25. This metallized surface also includes an aperture aligned with aperture 21. The aperture in layer 15 is designated 26.

The bottom layer comprises a metallic pad 16 adapted for external electrical connections by lead 27. The pad and lead are conveniently formed on insulating material designated 29. The insulating layers conveniently comprise printed circuit (PC) boards on which the metallic annulus, pad and leads are formed by silk screen or photolithographic techniques well known in the art.

An input signal, Vi, is applied to lead 23 by input means 30 during operation. An output signal, Vo, which is a function of the charge or voltage on test object 11, is applied to an output means 31. The output means in practice also provides for producing a voltage output in response to the signal Vo and a reference signal produced by a multilayered structure similar to that of FIG. 1 but without aperture 21. The output arrangement is represented in FIG. 2.

Figure 2:
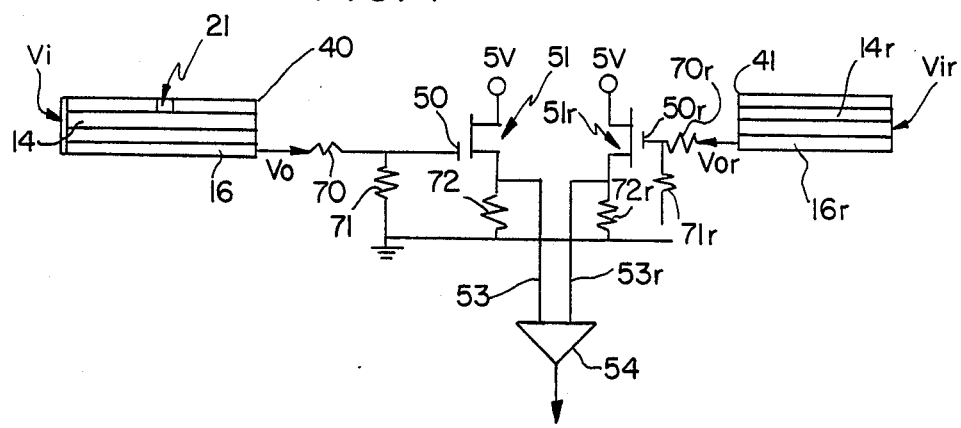
FIG. 2 is a schematic circuit diagram of the volt meter of FIG. 1 to a like reference arrangement for generating a signal representative of the charge or voltage on a test surface.

FIG. 2 represents the multilayered structure of FIG. 1 as a four layer composite 40 to which an input signal Vi is applied. The figure also represents a reference four layer composite 41 to which a like input signal Vir is applied. Note that the composite 40 includes aperture 21 and no such aperture is shown in composite 41. Also note that the metallized surfaces 20 and 25 of FIG. 1 are grounded. The corresponding elements of composite 41 also are grounded. Thus, the absence of an aperture (21) in composite 41 enables the output Vo+(from 41) to follow the input signal whereas the output Vo (from 40) follows both the input signal and the field from the test object in a manner to eliminate common mode noise.

FIG. 2 represents the active elements of FIG. 1 as layers 14 and 16 for the annulus and the sensor. Similarly it represents analogous elements of the reference composite 41 as 14r and 16r where the r stands for reference. The input signal Vi thus is applied to annulus 14 and the input reference signal Vir is applied to 14r. The output signals Vo and Vor are taken from 16 and 16r respectively. Those output signals are applied to the gates 50 and 50r of field effect transistors (FET's) 51 and 51r. The sources of FET's 51 and 51r are connected typically to a 5 volt source. The drains of the FET's are connected to first and second inputs 53 and 53r of a differential amplifier 54. Amplifier 54 provides a normalized output voltage adapted to drive a display (not shown) which could be a familiar volt meter indicator or may be adapted to drive a digital display or as an input to a computer for statistical analysis.

Figure 3:
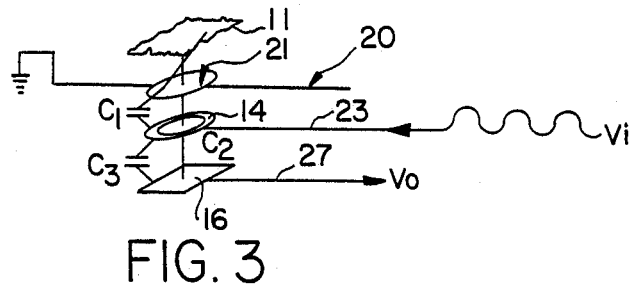
FIG. 3 is a schematic circuit diagram of the structure of FIG. 1.

The high frequency performance and diminutive size of the structure of FIG. 1 compared to prior art structures may be appreciated from a consideration of the schematic diagram of FIG. 3. The prior art achieved a variable capacitance by physically changing the distance between an input plate and the test object. This was accomplished by fixing the plate to a tuning fork, an arrangement requiring considerable space and input power. Further, the arrangement resulted in a circuit configuration which was unavoidably characterized by a long time constant and a low speed of operation. In contradistinction, the structure of FIG. 1 is adapted to apply a high frequency input signal to a plate which forms part of two capacitors, one with the test object and one with the sensor. The structure is adapted to define a third capacitor between the test object and he sensor. The arrangement permits the use of high ($10^{13}$) ohm resistors 70, 71 and 7y2 and 70r, 71r and 72r in FIG. 2 and a characteristic low time constant.

FIG. 3 designates the capacitor between the test object 11 and annulus 14 as C1. The figure designates the capacitor between the test object 11 and sensor 16 a C2 and the capacitor between annulus 14 and sensor 16 as C3. It is clear that the input signal Vi varies the voltage on annulus 14 and thus the voltage on the sensor whereas the field from the charge (or voltage) on the test object also affects the voltage on the sensor directly (via capacitor C2). The output signal is DC stable. Prior art devices were not DC stable because they could not be designed so that the charge bled off sufficiently fast. Specifically, prior art designs required the gate of an FET to be grounded via an impedance of about $10^{13}$ ohms which permitted equilibrium to be achieved in ten milliseconds. This lead to unreliable readings which could be remedied only with unachievable higher impedances. The use of a tuning fork overcame this problem only at the expense of slow operating speeds mentioned hereinbefore.

FIG. 4 shows the three capacitors of FIG. 3 along with the input circuit configuration in a practical arrangement with a reference structure. The input signal is operative to charge capacitor C1 affecting the charge on the test object if that object is metal. The input signal is applied via a high impedance network comprising resistors 90 and 91, the latter being connected to ground to provide for low current operation. The structure of FIG. 1 is adapted to measure the charge on one plate (the test object 11) of capacitors C1 and C2. A fixed charge Q can be measured. Alternatively, the voltage on the test object can be measured in an arrangement employing battery 94 and representative switch 95. The relationship between the test object and the sensor via the various capacitors may be understood from a consideration of broken blocks 100 and 101 representing the test object and the sensor respectively. It is clear that the charge or voltage on the test object influences capacitors C1 and C2 whereas the voltage across capacitor C2 and C3 determine the sensor voltage. It is also apparent that the input signal is applied to annulus 14 which constitutes a plate of both capacitors C1 and C3 as shown. The corresponding reference circuit is shown also in FIG. 4 and is operative in an analogous manner except that the absence of aperture 21 in the reference structure eliminates any possible contributions from the test object. FIGS. 5, 6 and 7 are graphs representing the voltage (V11) on the test object, the sensor voltage V16, and the differential amplifies voltage (V54) with respect to time. For a constant voltage of say one thousand volts on the test object as shown in FIG. 5, the sensor voltage follows the input voltage Vi but at lower amplitude as illustrated by curves 105+ and 105− in FIG. 6 superimposed on curve Vi shown in phantom. The output of the differential amplifier may be ten volts as shown in FIG. 7.

The entire structure of FIG. 1 can be made with the dimension of $\frac{1}{4}"\times\frac{1}{4}"$ /1/16". Even with the electronics of FIG. 2, the entire package could easily have the dimensions no greater than $\frac{1}{4}"\times\frac{1}{4}"\times\frac{1}{2}"$. Aperture 21 typically has a diameter of two millimeters and conveniently is adapted to test a surface spaced apart from the surface 20 (of FIG. 1) a like distance.

The volt meter of FIGS. 1 through 4 is operative because of the slight perturbation of the charge under test induced by the volt meter itself. This interaction makes the signal non linear so that the output is a product of the surface under test and the input signal.

In either embodiments, ground plane 15 may be omitted with perhaps even greater sensitivity achieved. To enhance sensitivity in any of the embodiments herein, the lead connection to 14 and to 16 should be oriented to minimize capacitive coupling therebetween and to reduce the length of the pads.

What is claimed is:

1. A lamellate structure comprising first, second, third and fourth layers electrically insulated from one another, said first layer being electrically conducting, said second layer including an annulus of electrically conducting material adapted for external electrical connection, said third layer also being electrically conducting, said fourth layer comprising a metallic pad positioned in registry with said annulus and being adapted for external electrical connection.

2. A lamellate structure in accordance with claim 1 wherein said first layer includes a first aperture in registry with said annulus.

3. A lamellate structure in accordance with claim 2 wherein said third layer includes a second aperture also in registry with said annulus.

4. A multilayered structure for providing an output signal representative of an electric field generated by a charge or a voltage on a test object, said structure comprising an input capacitor plate for receiving an input signal, said structure also comprising an output capacitor plate for applying an output signal to an output means, said input and output plates defining a first capacitor, said input and output capacitor plates respectively defining second and third capacitors with a test object in close proximity therewith, said input capacitor plate comprising a metallic annulus.

5. A multilayered structure in accordance with claim 4 wherein said output plate comprises a metallic pad aligned with said annulus, said pad being positioned in a plane parallel to and spaced apart in a first direction from a plane defined by said annulus.

6. A multilayered structure in accordance with claim 5 also including a metallized layer in a plane parallel to and spaced apart in a second direction from said plane of said annulus.

7. A multilayered structure in accordance with claim 6 wherein said metallized layer includes an aperture.

* * * * *